(12) United States Patent
Knowlton et al.

(10) Patent No.: US 9,144,464 B2
(45) Date of Patent: Sep. 29, 2015

(54) COMPOSITE FOR PACKAGING A MEDICAL DEVICE AND METHOD OF FORMING THE SAME

(75) Inventors: David Knowlton, Tewksbury, MA (US); Daniel J. Shaw, Jr., Groveland, MA (US)

(73) Assignee: UFP TECHNOLOGIES, INC., Georgetown, MA (US)

( * ) Notice: Subject to any disclaimer, the term of this patent is extended or adjusted under 35 U.S.C. 154(b) by 0 days.

(21) Appl. No.: 12/857,409

(22) Filed: Aug. 16, 2010

(65) Prior Publication Data

US 2011/0036736 A1 Feb. 17, 2011

Related U.S. Application Data

(60) Provisional application No. 61/234,167, filed on Aug. 14, 2009.

(51) Int. Cl.
| | |
|---|---|
| *B32B 1/02* | (2006.01) |
| *A61B 19/02* | (2006.01) |
| *B32B 1/08* | (2006.01) |
| *A61B 17/00* | (2006.01) |
| *B29C 49/04* | (2006.01) |
| *B29C 49/22* | (2006.01) |
| *B29C 51/08* | (2006.01) |
| *B29C 51/14* | (2006.01) |
| *B29K 23/00* | (2006.01) |
| *B29K 27/06* | (2006.01) |
| *B29K 67/00* | (2006.01) |
| *B29K 69/00* | (2006.01) |
| *B29K 75/00* | (2006.01) |
| *B29K 81/00* | (2006.01) |
| *B29K 105/00* | (2006.01) |

(52) U.S. Cl.
CPC .......... *A61B 19/026* (2013.01); *A61B 19/0271* (2013.01); *A61B 2017/00526* (2013.01); *A61B 2019/0219* (2013.01); *A61B 2019/0267* (2013.01); *A61B 2019/0268* (2013.01); *B29C 49/04* (2013.01); *B29C 49/22* (2013.01); *B29C 51/082* (2013.01); *B29C 51/14* (2013.01); *B29K 2023/065* (2013.01); *B29K 2023/0633* (2013.01); *B29K 2023/12* (2013.01); *B29K 2027/06* (2013.01); *B29K 2067/00* (2013.01); *B29K 2069/00* (2013.01); *B29K 2075/00* (2013.01); *B29K 2081/06* (2013.01); *B29K 2105/005* (2013.01); *B29K 2105/0026* (2013.01); *B29K 2105/0032* (2013.01); *B29K 2105/0044* (2013.01); *Y10T 156/1048* (2015.01)

(58) Field of Classification Search
USPC .................... 428/34.1, 34.2, 35.7, 35.9, 36.9
See application file for complete search history.

(56) References Cited

U.S. PATENT DOCUMENTS

| 3,028,345 | A | * | 4/1962 | Johnson | ......................... | 521/125 |
| 3,502,239 | A | * | 3/1970 | Worboys et al. | .......... | 220/560.15 |
| 3,725,120 | A | * | 4/1973 | Suter | ........................... | 428/424.6 |

(Continued)

*Primary Examiner* — Marc Patterson
(74) *Attorney, Agent, or Firm* — Howard & Howard Attorneys PLLC

(57) ABSTRACT

A composite for packaging a medical device has a first layer including an aromatic polyether polyurethane and a second layer. The first layer forms a base that has a plurality of walls extending therefrom to define a cavity for receiving the medical device. The second layer is disposed on the first layer opposite the cavity. The composite is formed from a method that includes the step of disposing the first layer on the second layer. The composite may also be included with a container to form a packaging system.

11 Claims, 6 Drawing Sheets

(56) References Cited

U.S. PATENT DOCUMENTS

| | | | |
|---|---|---|---|
| 3,984,359 A * | 10/1976 | Collins et al. | 521/167 |
| 4,654,240 A | 3/1987 | Johnston | |
| 4,750,619 A | 6/1988 | Cohen et al. | |
| 5,061,534 A | 10/1991 | Blemberg et al. | |
| 5,093,164 A | 3/1992 | Bauer et al. | |
| 5,395,681 A | 3/1995 | Hargarter et al. | |
| 5,690,226 A | 11/1997 | N'Guyen | |
| 5,756,170 A * | 5/1998 | Licht et al. | 428/35.7 |
| 5,916,685 A | 6/1999 | Frisk | |
| 6,150,004 A | 11/2000 | Oikawa et al. | |
| 6,218,017 B1 | 4/2001 | Yamashita et al. | |
| 6,337,113 B1 | 1/2002 | Muggli et al. | |
| 6,569,533 B1 * | 5/2003 | Uchida et al. | 428/423.1 |
| 6,586,091 B2 | 7/2003 | Iijima et al. | |
| 6,589,616 B2 | 7/2003 | Muggli et al. | |
| 6,589,642 B1 | 7/2003 | Miller et al. | |
| 6,592,978 B1 | 7/2003 | Miller et al. | |
| 6,777,524 B1 * | 8/2004 | Shimizu et al. | 528/76 |
| 6,830,149 B2 | 12/2004 | Merboth et al. | |
| 6,902,645 B2 | 6/2005 | Miller | |
| 7,205,046 B2 | 4/2007 | Kobayashi et al. | |
| 7,214,414 B2 | 5/2007 | Khemani et al. | |
| 7,297,394 B2 | 11/2007 | Khemani et al. | |
| 7,429,417 B2 | 9/2008 | Kobayashi et al. | |
| 2002/0188065 A1 | 12/2002 | Kelch | |
| 2003/0017328 A1 | 1/2003 | Inoue et al. | |
| 2003/0148124 A1 * | 8/2003 | Yamada et al. | 428/474.4 |
| 2004/0069157 A1 | 4/2004 | Lin | |
| 2004/0131863 A1 * | 7/2004 | Belliveau et al. | 428/423.1 |
| 2007/0014977 A1 | 1/2007 | Graney et al. | |

* cited by examiner

FIG. 5
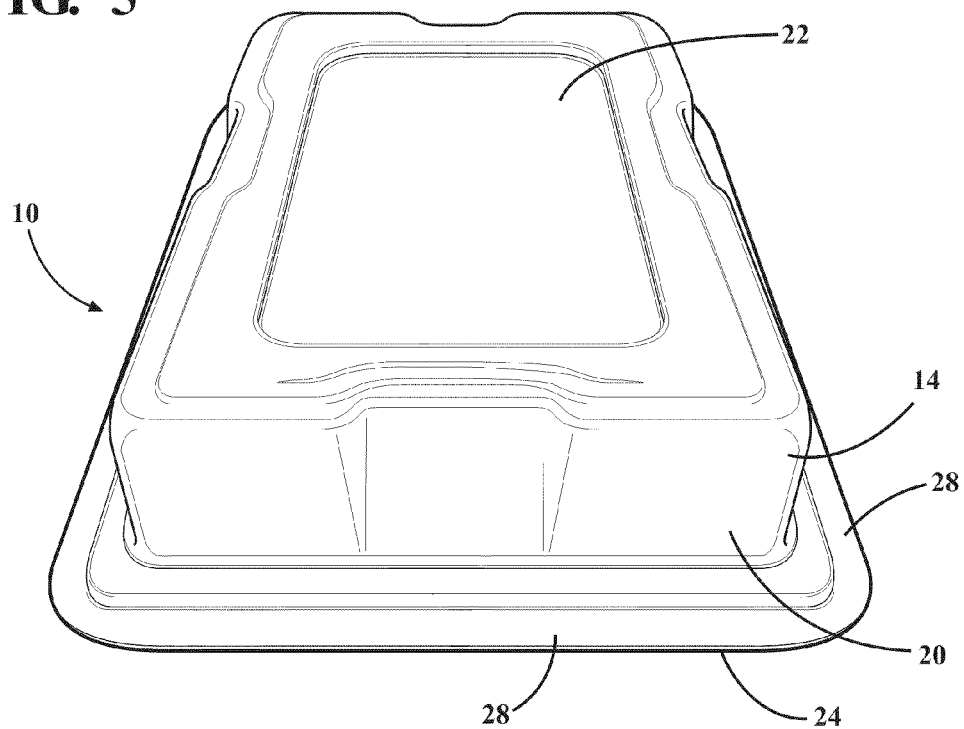
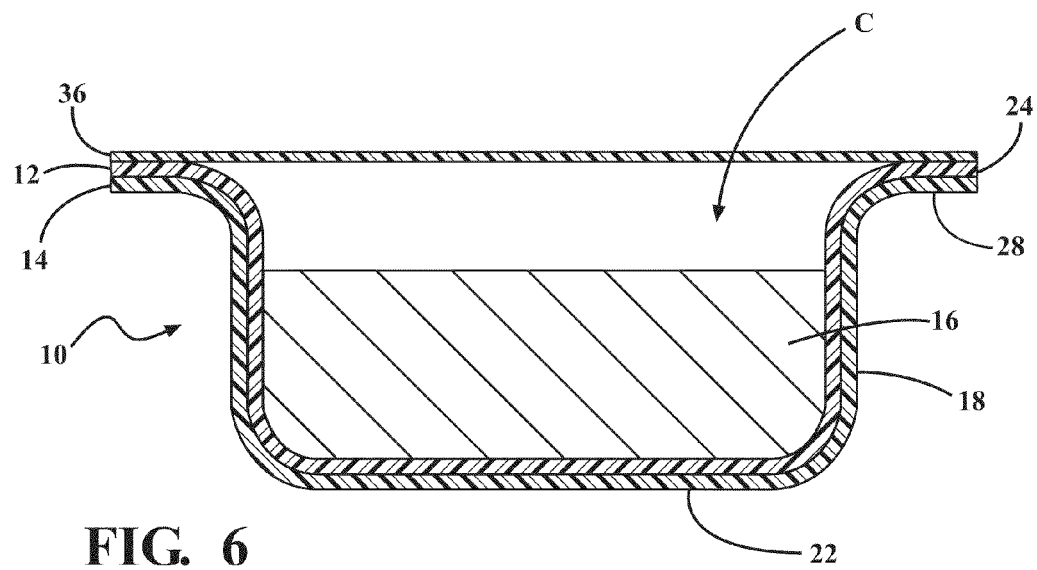
FIG. 6

COMPOSITE FOR PACKAGING A MEDICAL DEVICE AND METHOD OF FORMING THE SAME

CROSS-REFERENCE TO RELATED APPLICATION

This application claims priority under 35 U.S.C. 119 from Provisional Patent Application Ser. No. 61/234,167 filed Aug. 14, 2009, the disclosure of which is incorporated in its entirety by reference.

FIELD OF THE INVENTION

The subject invention generally relates to a composite for packaging a medical device and a method of forming the composite. More specifically, the subject invention relates to a composite that includes a first layer including an aromatic polyether polyurethane and a second layer that is disposed on the first layer.

DESCRIPTION OF THE RELATED ART

It is well known in the art to package medical devices in a variety of containers. These containers are typically designed to closely house the medical device. In other words, the medical device is typically packaged in very close contact with the containers to secure the device for shipping, sterilization, and use. Some containers include polyethylene cross-linked foam and glycol-modified polyethylene terephthalate (PETG) because these compounds tend to be clear, easily sterilized, and cost effective. However, many medical devices, such as those used to replace knee joints and hip joints, have one or more rough fixation surfaces. These rough surfaces typically have a coating formed from hydroxyl apatite. These rough surfaces tend to abrade the containers thereby creating undesirable shavings which contaminate the devices. Once abraded, the containers tend to lose rigidity and allow the devices to shift and move during shipping, sterilization, and use, all of which are undesirable. Furthermore, any coating on the rough surfaces can be rubbed off and removed.

In an attempt to minimize abrasion of the containers, and minimize removal of any coatings, efforts have been made to house medical devices in bags or pouches which are then disposed in the containers. Although the bags and pouches resist abrasion, their use increases production costs and processing complexities. In addition, the bags and pouches can be resistant to sterilization techniques which also increases costs, processing times, and overall suitability of use. Moreover, the bags and pouches do not provide non-slip surfaces to hold the devices in place in the containers. This tends to contribute to the shifting and moving of the devices in the containers during shipping, sterilization, and use. Accordingly, there remains an opportunity to develop an improved package for medical devices.

SUMMARY OF THE INVENTION AND ADVANTAGES

The present invention provides a composite for packaging a medical device. The composite includes a first layer including an aromatic polyether polyurethane and a second layer. The first layer forms a base having a plurality of walls. The plurality of walls extend from the base to define a cavity for receiving the medical device. The second layer is disposed on the first layer opposite the cavity.

The composite has increased abrasion resistance which tends to reduce abrasion and generation of shavings. Additionally, the composite tends to maintain rigidity and inhibit slippage which reduces shifting of the medical device during shipping, sterilization, and use. Further, the composite is thermo-formable, heat sealable, and can be sterilized using various methods which reduces costs and processing times.

BRIEF DESCRIPTION OF THE SEVERAL VIEWS OF THE DRAWINGS

Other advantages of the present invention will be readily appreciated, as the same becomes better understood by reference to the following detailed description when considered in connection with the accompanying drawings wherein:

FIG. 5 is a bottom end perspective view of an additional embodiment of the composite;

FIG. 6 is a side cross-sectional view of one embodiment of the composite;

DETAILED DESCRIPTION OF THE INVENTION

Figure 1:
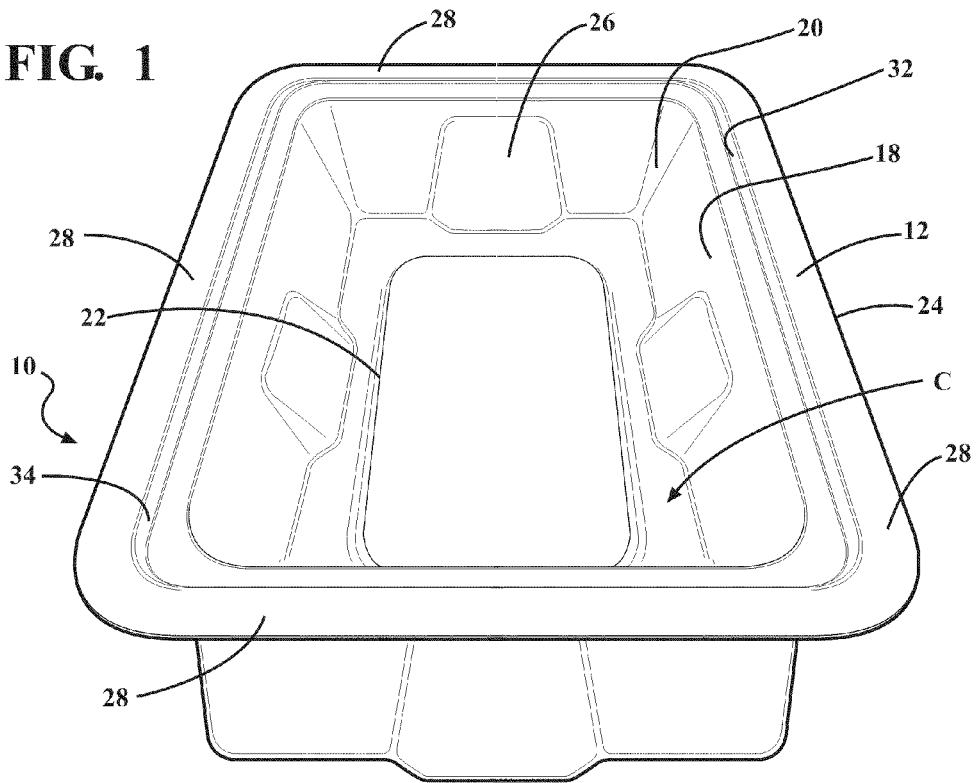
FIG. 1 is a top end perspective view of one embodiment of the composite.
Figure 2:
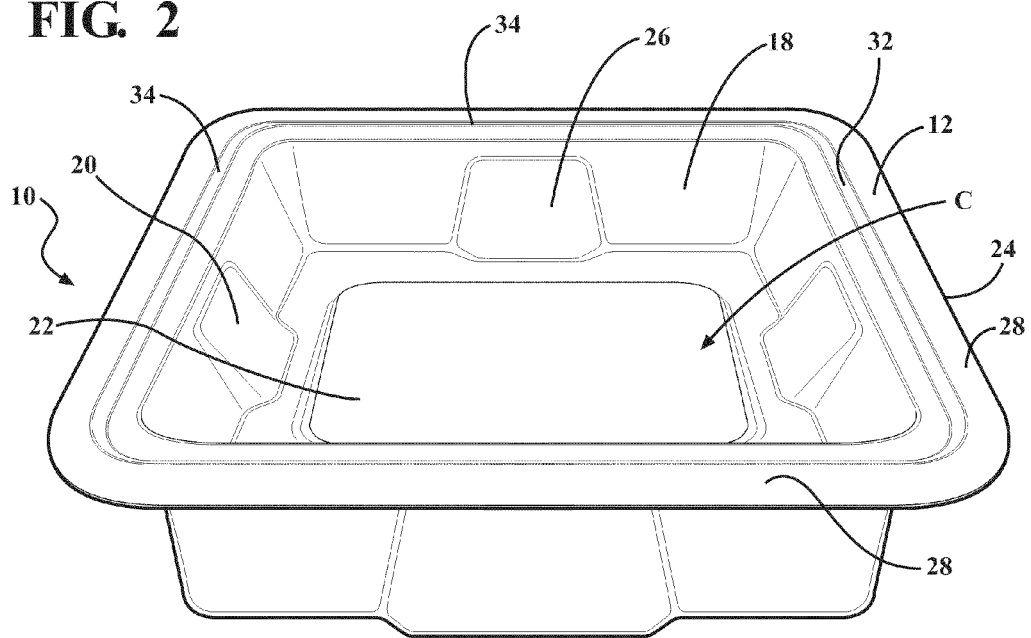
FIG. 2 is a top side perspective view of another embodiment of the composite.
Figure 3:
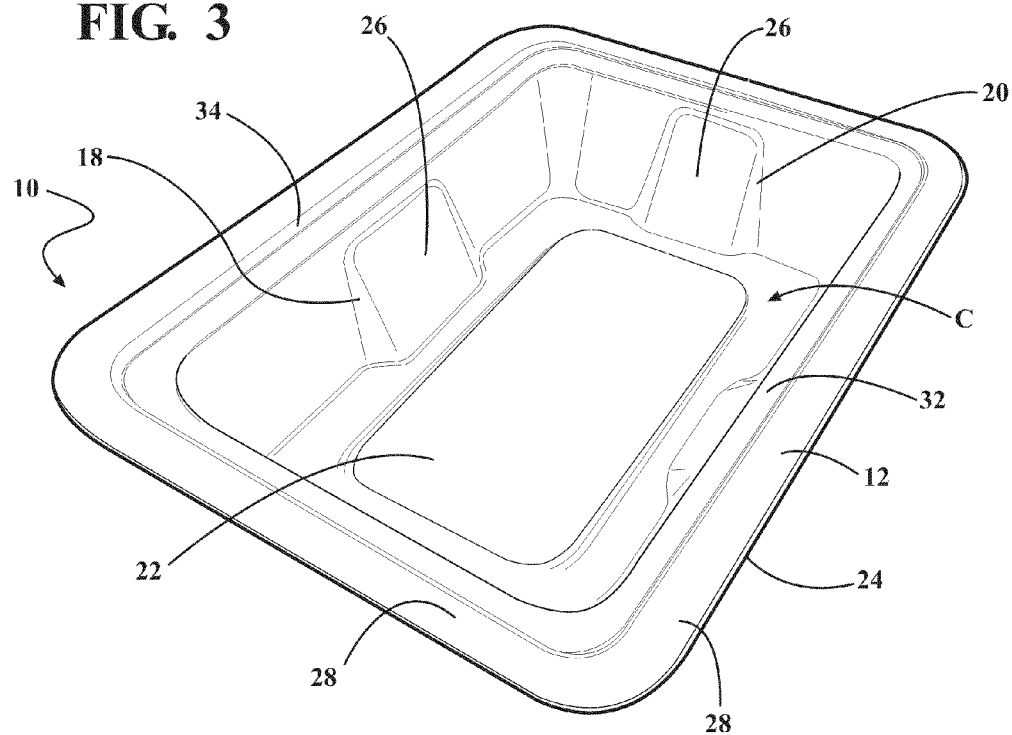
FIG. 3 is a top angled perspective view of yet another embodiment of the composite.
Figure 4:
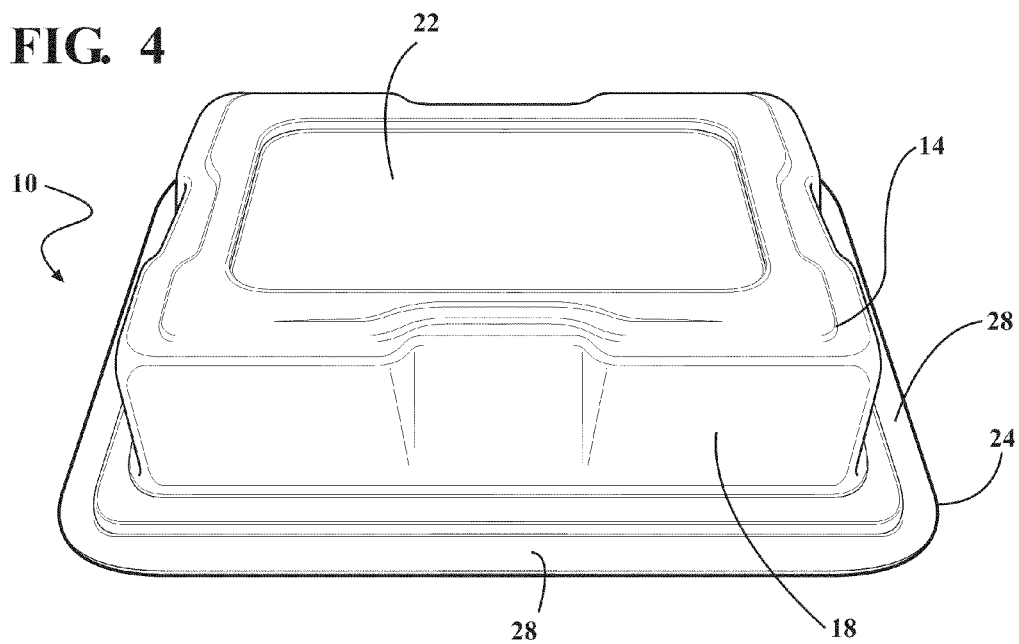
FIG. 4 is a bottom side perspective view of still another embodiment of the composite.

A composite (10) for packaging a medical device (16) is shown in FIGS. 1-8. The composite (10) may be further defined as a film, container, box, carton, bag, envelope, drum, can, bottle, or the like. In FIGS. 1-5 and 9, the composite (10) is further defined as a carton. In one embodiment, the composite (10) is further defined as a multi-layer film. In another embodiment, as set forth in FIG. 6, the composite (10) has two layers. The composite (10) may be sealed to itself or, alternatively, may be sealable to itself or sealable to an external substrate by any means known in the art including, but not limited to, manual sealing (e.g. with a fastener, clip, or string) and/or chemical sealing (e.g. with melt-adhesion or chemical fusion).

The medical device (16) may be any known in the art and may have any shape and size. The medical device (16) may be, but is not limited to, a medical implant. Suitable examples of medical implants include, but are not limited to, hip implants, knee implants, ankle implants, dental implants, allografts, and the like. The medical device (16) may be formed from any composition including, but not limited to, metals, ceramics, biomaterials, apatite, and combinations thereof. Typically, the medical device (16) includes one or more surfaces. In one embodiment, these surfaces are coated with hydroxyl apatite. These surfaces are commonly referred to in the art as "fixation surfaces." In one embodiment, the medical device (16) is a hip implant. In another embodiment, the medical device (16) is a knee implant. In other embodiments, the medical device (16) is further defined as one of orthopedic (e.g. maxillofacial) implants, re-constructive prostheses, cardiac prostheses, joint implants, skin implants, dental implants, corneal implants, subcutaneous drug delivery devices such as medical implantable pills, drug-eluting stents, and the like. In yet other embodiments, the medical device (16) is further defined as a trauma device, surgical tool, plate, surgical fixation device, surgical accessory, or the like. The surgical fixation device may include, but is not limited to, screws, pins, and fasteners. It is contemplated that the medical device (16) may be simultaneously classified as more than one of the aforementioned types.

As shown in FIG. 6, the composite (10) includes a first layer (12) and a second layer (14). The first layer (12) is an innermost layer of the composite (10). In other words, the first layer (12) is an interior layer of the composite (10) that typically directly contacts the medical device (16). Of course, the composite (10) itself does not necessarily include the medical device (16) and the terminology "directly contacts the medical device (16)" refers to a design or ability of the first layer (12) to be in direct contact with the medical device (16) when the composite (10) is in use. However, in use, the composite (10) typically includes the medical device (16).

In various embodiments, the medical device (16) is at least partially disposed within a protective cover before being placed in the composite (10). The protective cover is not limited in composition, shape, or design. In one embodiment, the protective cover is further defined as a bag (e.g. a thermoplastic polyurethane bag) and the medical device (16) is placed inside of the bag. Alternatively, the protective cover may be further defined as a three dimensional foam in which the medical device (16) may be placed. In one embodiment, both a bag and a three dimensional foam are utilized. The medical device (16) and the protective cover may then be disposed within the composite (10) such that the first layer (12) of the composite (10) may be in direct contact with the protective cover.

The first layer (12) of the composite (10) includes an aromatic polyether polyurethane. Without intending to be bound by any particular theory, it is believed that the aromatic polyether polyurethane may create a non-slip surface that aids in cradling or restraining the medical device (16) in the composite (10). The aromatic polyether polyurethane is also typically abrasion resistant. The aromatic polyether polyurethane also, in part, provides protection to the composite (10) if the composite is dropped, is impacted, or is contacted with force. Typically, the aromatic polyether polyurethane is impact resistant and minimizes or prevents shattering, fragmentation, and/or breaking apart of the composite (10) upon impact. A particularly suitable aromatic polyether polyurethane is commercially available from Deerfield Urethane under the trade name of Dureflex®. However, the composite (10) is not limited to use of this aromatic polyether polyurethane. The aromatic polyether polyurethane may be a rigid or flexible foam or may be an elastomer or a thermoplastic polyurethane. Alternatively, the first layer (12) may include a mixture of rigid foams, flexible foams, elastomers, and/or thermoplastic polyurethanes. In one embodiment, the aromatic polyether polyurethane is further defined as a film. In another embodiment, the aromatic polyether polyurethane is further defined as a sheet.

As is known in the art, aromatic polyether polyurethanes are typically formed from the reaction of a polyol and an isocyanate. For purposes of this invention, any suitable polyol and any suitable isocyanate may be used to form the aromatic polyether polyurethane. Typically, the polyol is further defined as a polyether polyol (i.e., a polyetherol). The polyether polyol may be aromatic or aliphatic. Alternatively, more than one polyol may be used to form the aromatic polyether polyurethane. A first polyol may be an aromatic polyether polyol and a second polyol may be an aliphatic polyether polyol. Similarly, the isocyanate may be further defined as an aromatic isocyanate or an aliphatic isocyanate. It is contemplated that more than one isocyanate may be used to form the aromatic polyether polyurethane. In one embodiment, an aromatic isocyanate and an aliphatic isocyanate are used to form the aromatic polyether polyurethane.

In various embodiments, the aromatic polyether polyurethane typically has the following physical properties, ±1%, 5%, 10%, 15%, 20%, or 25%, that are measured according to the described standardized tests. However, it is to be appreciated that the aromatic polyether polyurethane is not limited to the following physical properties and may include physical properties that are not described below or physical properties that may be different by more than ±1%, 5%, 10%, 15%, 20%, or 25% from those described below. Furthermore, the physical properties of the aromatic polyether polyurethane may be determined using standardized tests different from those described below.

| | |
|---|---|
| Specific Gravity (ASTM D-792) | 1.12 |
| Shore A Durometer Hardness (ASTM D-2240) | 87 |
| Ultimate Tensile Strength (ASTM D-882) | 10,000 psi |
| Ultimate Elongation (ASTM D-882) | 575% |
| 100% Modulus (ASTM D-882) | 1150 psi |
| 300% Modulus (ASTM D-882) | 2700 psi |
| Tear Resistance (ASTM D-1004) | 500 pli |
| Minimum Softening Point (ASTM E2347-04) | 150° C. |
| Maximum Softening Point (ASTM E2347-04) | 170° C. |
| Approximate Yield | 172 sq. ft/lb at 1 mil |

In one embodiment, the aromatic polyether polyurethane has a specific gravity of from 0.84 to 1.40 measured according to ASTM D-792.

In another embodiment, the aromatic polyether polyurethane a shore A hardness of from 66.25 measured according to ASTM D-2240 to a shore D hardness of 70.00.

In yet another embodiment, the aromatic polyether polyurethane has an ultimate tensile strength of from 7,500 to 12,500 psi, an ultimate elongation of from 431.25% to 718.75%, a 100% modulus of from 862.5 to 1437.5 psi, and a 300% modulus of from 2025 to 3375 psi, each measured according to ASTM D-882.

In still yet another embodiment, the aromatic polyether polyurethane has a tear resistance of from 375 to 625 pli measured according to ASTM D-1004.

In still yet another embodiment, the aromatic polyether polyurethane has a minimum softening point of from 112.5 to 187.5° C. and a maximum softening point of from 127.5 to 212.5° C. measured according to ASTM E2347-04.

In one embodiment, the first layer (12) includes the aromatic polyether polyurethane described above and a second polyurethane. The second polyurethane is not particularly limited any may be any polyurethane known in the art. The second polyurethane may be a second aromatic polyether polyurethane that is different from the aromatic polyether polyurethane first introduced above. In another embodiment, the second polyurethane is a polyester polyurethane. Alternatively, the first layer (12) may include the aromatic polyether polyurethane described above and one or more additional polyether and/or polyester polyurethanes.

In one embodiment, the first layer (12) consists essentially of the aromatic polyether polyurethane. In this embodiment, the terminology "consists essentially of" limits the first layer (12) from including any other polymer or compound that materially affects the basic and novel characteristics of the first layer (12). Typically, in this embodiment, the first layer (12) does not include any other polyurethanes, especially aromatic polyether polyurethanes. Alternatively, the first layer (12) may consist of the aromatic polyether polyurethane.

Typically, the first layer (12) is square or rectangular but may be of any shape and size. The first layer (12) typically has a thickness of from 0.5 to 250, more typically of from 1 to 60, still more typically of from 1 to 30, and most typically of from 2 to 30, mils. In other embodiments, the first layer (12) has a thickness of from 1 to 10 mils or from 2 to 10 mils. However, the instant composite (10) is not limited to these thicknesses. It is contemplated that the first layer (12) may have any thickness or range of thicknesses within the above ranges as determined by one of skill in the art. Typically, a thickness of the first layer (12) is correlated to a size, density, and/or weight of the medical device (16) to be used. However, the instant composite (10) is not limited to such a correlation. In one embodiment, the first layer (12) has a variable thickness of from 2 to 10 mils and may have segments of differing thicknesses. The first layer (12) may also be of any color, may be clear, opaque, or transparent. The first layer (12) may also be smooth or rough or have any texture known in the art.

Referring back to the second layer (14), the second layer (14) is disposed on the first layer (12), as shown in FIG. 6. Typically, no adhesive is disposed between the first and second layer (12, 14). In one embodiment, the second layer (14) is an outermost layer of the composite (10), i.e., forms at least a portion of an exterior of the composite (10) that is exposed to the environment. It is to be understood that the second layer (14) may be disposed in direct contact with the first layer (12) or may be disposed apart from the first layer (12) and still be disposed "on" the first layer (12). In one embodiment, the composite (10) includes more than two layers and the second layer (14) is an interior layer of the composite (10) (not shown in the Figures) that is not exposed to the environment.

The second layer (14) may be soft and flexible or may be rigid and stiff. Alternatively, the second layer (14) may include rigid and stiff segments while simultaneously including soft and flexible segments. The second layer (14) may be load bearing or non load bearing and may be included in any portion of the composite (10). The second layer (14) may be a "top layer," also known as a superstrate, or a "bottom layer", also known as a substrate, of the composite (10). The second layer (14) typically functions as a load-bearing substrate that is an outermost layer of the composite (10). The second layer (14) also provides protection and impact resistance to the composite (10) but may crack or fragment upon impact. Typically, the second layer (14) is impact resistant and minimizes or prevents shattering, fragmentation, and/or breaking apart of the composite (10) upon impact. In one embodiment, the second layer (14) may crack but the aromatic polyether polyurethane (of the first layer (12)) remains intact and resists cracking to maintain the integrity (and sterility) of the composite (10).

The second layer (14) is not particularly limited in composition and may include one or more of a plastic, an organic polymer, an inorganic polymer, and combinations thereof. In various embodiments, the second layer (14) includes one or more of acrylics, polyesters, silicones, polyurethanes, halogenated plastics, polystyrenes, polyvinylchlorides, polyethylene terephthalate glycols (PETG), polychlorotrifluoroethylenes (PCTFE), low-density polyethylenes, high-density polyethylenes, cross-linked, high-density polyethylenes, polyethylene foams, polycarbonates, polysulfones, fluorinated ethylene polypropylenes, ethylene-tetrafluoroethylenes, ethylene-chlorotrifluoroethylene copolymers, perfluoroalkyl plastics, polypropylenes, cyclic olefin copolymers (COCs), and combinations thereof. In one embodiment, the second layer (14) includes PETG. In another embodiment, the second layer (14) includes a "breathable" foam, as known in the art.

In other embodiments, the second layer (14) consists essentially of an organic polymer, such as PETG. In this embodiment, the terminology "consists essentially of" limits the second layer (14) from including any other polymer or compound that materially affects the basic and novel characteristics of the second layer (14). Alternatively, the second layer (14) may consist of the organic polymer, e.g. consist of PETG.

The second layer (14) typically has a thickness of from 0.5 to 250, more typically of from 1 to 70, still more typically of from 1 to 60, and most typically of from 20 to 60, mils. In other embodiments, the second layer (14) has a thickness of from 10 to 70 mils or from 10 to 60 mils. However, the instant composite (10) is not limited to these thicknesses. It is contemplated that the second layer (14) may have any thickness or range of thicknesses within the above ranges as determined by one of skill in the art. In one embodiment, the second layer (14) has a variable thickness of from 20 to 60 mils. It is contemplated that the thickness of the second layer (14) may vary with the type of medical device (16) used with the instant composite (10). The second layer (14) may also be of any color, may be clear, opaque, or transparent. The second layer (14) may also be smooth or rough or have any texture known in the art.

It is also contemplated that the composite (10) may include one or more additional layers that are independent from the first and second layers (12, 14). The one or more additional layers may be the same or different from the first and second layers (12, 14) and are not limited in their orientation in the composite (10).

The first layer (12) forms a base (22) having a plurality of walls extending therefrom, typically including side walls (18) and end walls (20), and a periphery (24) (e.g. an edge) of the composite (10), as shown in FIGS. 1-5. The plurality of walls (e.g. side and/or end walls (18, 20)) may define one or more projections (26) which may engage the medical device (16) to retain its position in the composite (10). Typically, the side walls (18), end walls (20), and base (22) define a rectangular plan form but may define any shape plan form known in the art.

Figure 7:
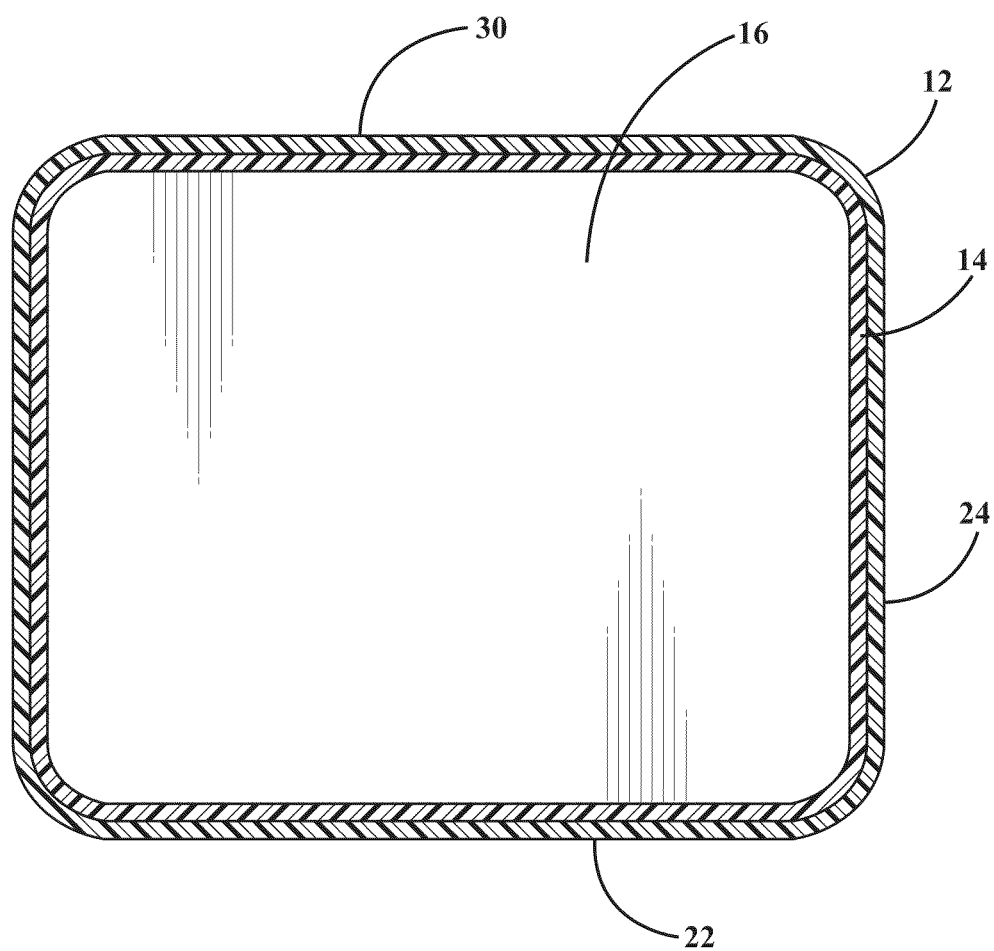
FIG. 7 is a side cross-sectional view of another embodiment of the composite.

The plurality of walls (e.g. side walls (18) and end walls (20)) and the base (22) define a cavity (C). The cavity (C) may be open faced or entirely enclosed (i.e., defined on all sides (44)) by the side walls (18), end walls (20), and base (22). The second layer (14) is disposed on the first layer (12) opposite the cavity (C). The first and second layers (12, 14) may also form a top (30), as shown in FIG. 7, to entirely enclose the cavity (C). The cavity (C) may be defined as any shape including, but not limited to, cylindrical shapes, spherical shapes, conical shapes, rectangular shapes, cubic shapes, and the like. In one embodiment, the cavity (C) is defined as a shape that is the same as, substantially similar to, or complementary to, the shape of the medical device (16). In another embodiment, the cavity (C) is defined as a pocket. Typically the cavity receives the medical device.

The plurality of walls (e.g. side walls (18) and/or end walls (20)) may define top portions ending in flat or planar flanges (28) which are substantially parallel to the base (22). In one embodiment, a stepped recess (32) is formed in one or more of the flanges (28) and is disposed around the cavity (C). The stepped recess (32) typically includes a recess periphery (e.g. an edge of the stepped recess) (34) that is beveled upward to the flanges (28) which may support a lid (36).

Figure 8:
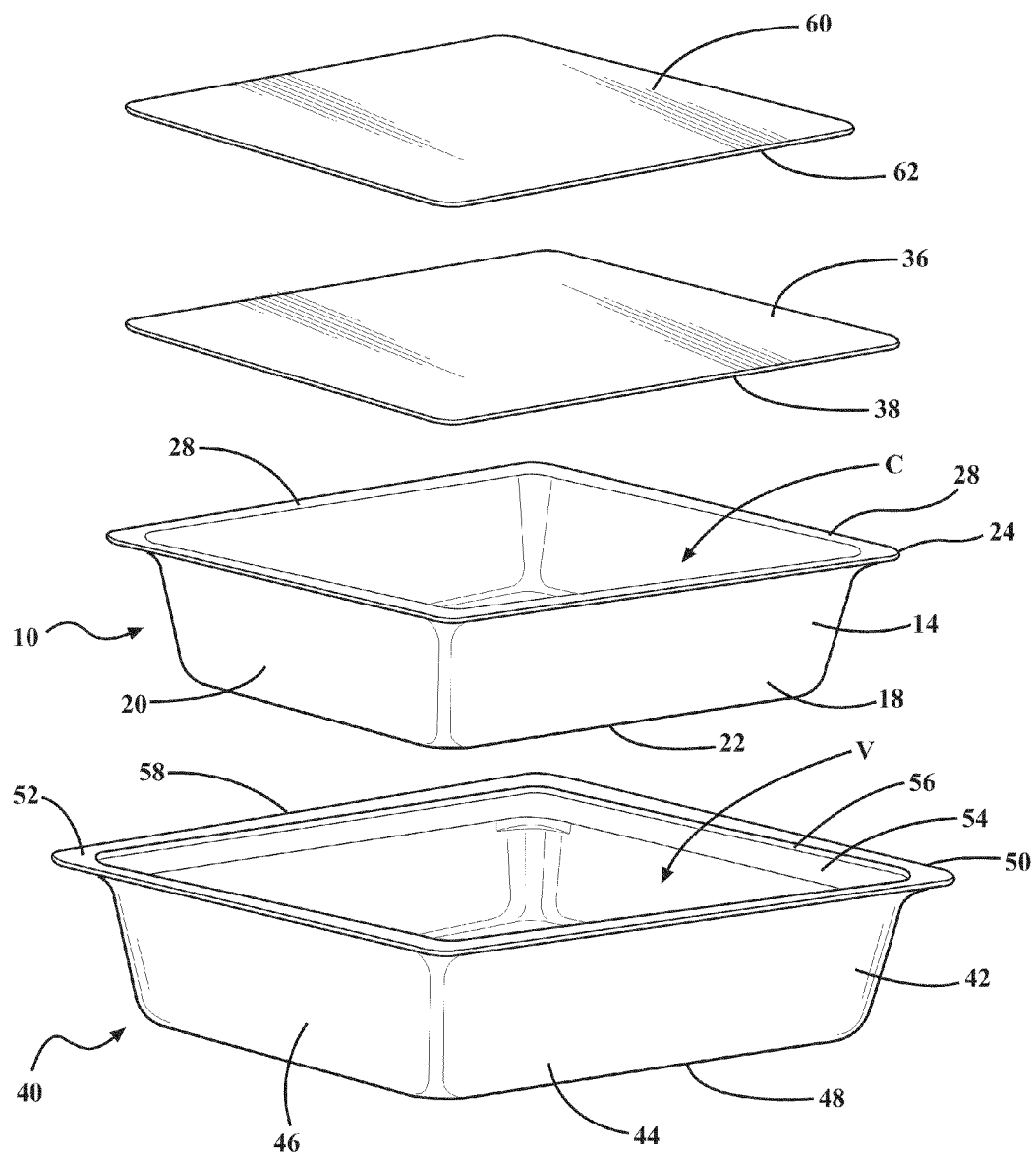
FIG. 8 is a side perspective view of an outer container and the composite.
Figure 9:
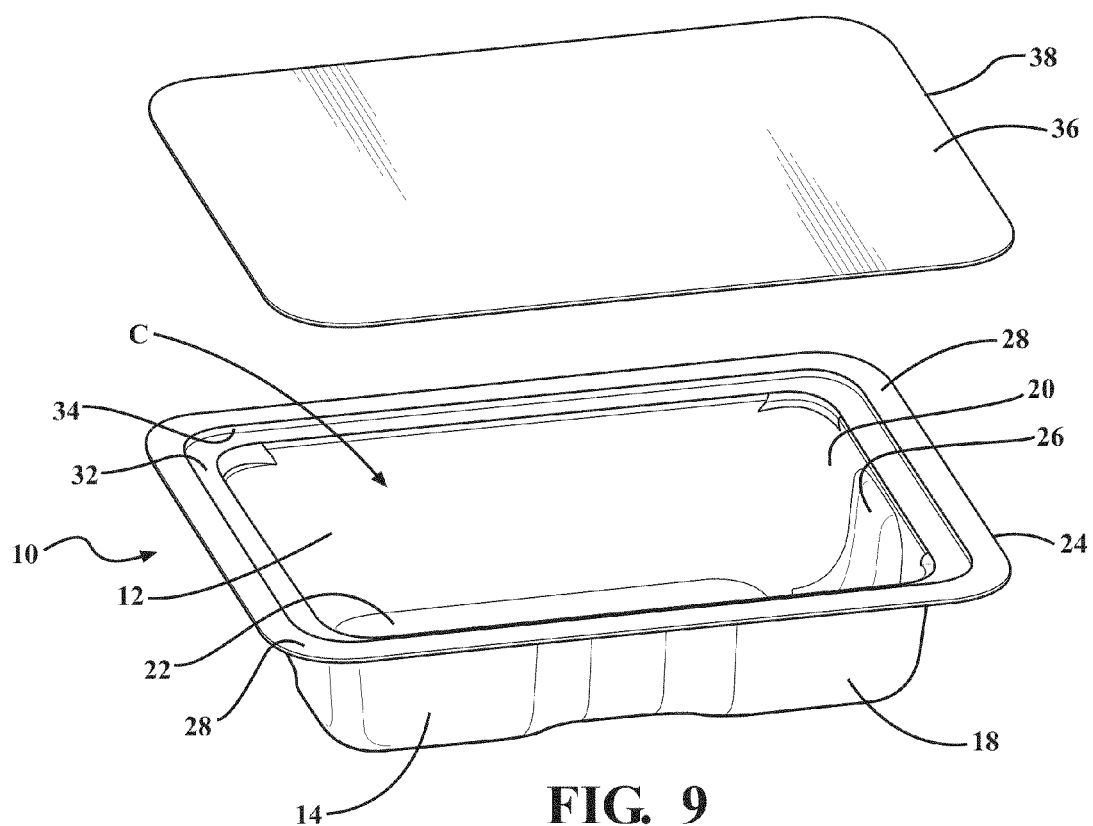
FIG. 9 is a side perspective view of another embodiment of the composite including a lid.

The lid (36) typically has a peripheral edge (38) and is typically disposed on the flanges (28), as shown in FIG. 8. The lid (36) may be sized and configured to cover the recess periphery (34) and the stepped recess (32) and the cavity (C) either in part or in their entirety. In one embodiment, the lid (36) is disposed such that the peripheral edge of the lid (38) aligns with the periphery (24) of the composite (10). In another embodiment, the lid (36) is disposed such that the peripheral edge of the lid (38) does not align with the periphery (24) of the composite (10). In this embodiment, the lid (36) is typically larger than or extends beyond the periphery (24) of the composite (10). The lid (36) is typically formed a suitable material in the art that can withstand sterilization with heat, chemicals, and/or radiation (e.g. ethylene oxide, gamma, e-beam, and/or peroxides). Suitable materials include, but are not limited to, a high density polyethylene such as Tyvek®, a combination of Tyvek® and polyethylene, Surlyn®, a combination of Surlyn® and Tyvek®, metal foils, polymer films, polyvinyl chloride (PVC), polychlorotrifluoroethylene (PCTFE), cyclic olefin copolymers (COCs), and combinations thereof. Typically, the lid (36) is formed from Tyvek®. Of course, the composite (10) is not limited to the aforementioned materials. The lid (36) typically has a thickness of from 1 to 60 mils but is not limited to this thickness. The lid (36) may have any thickness as chosen by one of skill in the art. The lid (36) may also be of any color, may be clear, opaque, or transparent. The lid (36) may also be smooth or rough or have any texture known in the art.

The lid (36) is typically adhered to the flanges (28) through use of an adhesive. The adhesive may be any known in the art and is not particularly limited. The adhesive may also have any thickness, as chosen by one of skill in the art.

Each of the layers of the composite (10) may independently and optionally include one or more conventional additives whose uses are well known to those skilled in the art. The use of such additives may be desirable in enhancing formation of the composite (10). Examples of such additives include oxidative and thermal stabilizers, impact modifiers such as thermoplastic olefins, thermoplastic elastomers, styrene butadiene rubber, lubricants, release agents, flame-retarding agents, oxidation inhibitors, oxidation scavengers, neutralizers, antiblock agents, dyes, pigments and other coloring agents, ultraviolet light absorbers and stabilizers, organic or inorganic fillers including particulate and fibrous fillers, reinforcing agents, nucleators, plasticizers, waxes, hot melt adhesives, biodegradation promoters, and combinations thereof. These additives may be used in any amount in any of the layers as determined by one of skill in the art.

In one embodiment, the composite (10) is further defined as a blister. As is known in the art, "blisters" or "blister packages" typically include a cavity defined by a polymer "web" and a lidding material that seals the cavity. The polymer "web" is typically formed by the first and second layers (12, 14) while the "lidding material" is typically defined as the lid (36). However, the instant composite (10) is not limited to these terms of art.

The composite (10) (e.g. the blister) is typically formed by a method that includes the step of disposing the first layer (12) on the second layer (14). The first layer (12) may be disposed on the second layer (14) by any means known in the art. Typically, the step of disposing the first layer (12) on the second layer (14) is further defined as thermoforming. Thermoforming typically includes any process involving heat, including but not limited to, laminating, radio frequency welding, ultrasonic welding, and co-extrusion. In another embodiment, the first layer (12) or the second layer (14) is die cut. However, the instant composite (10) is not limited to use of these techniques. Typically, thermoforming includes an automatic high speed positioning of a sheet or film of the composite (10) having an accurately controlled temperature into a pneumatically actuated forming station whereby a shape of the sheet or film is defined by a mold. The sheet or film, after positioned, may be trimmed or cut, as is known in the art. The thermoforming may utilize a variety of techniques including, but not limited to, use of a drape, vacuum, pressure, matched die, billow drape, vacuum snap-back, billow vacuum, plug assist vacuum, reverse draw with plug assist, trapped sheet, slip, diaphragm, twin-sheet cut sheet, and combinations thereof. The thermoforming may also utilize a free-blowing technique, a pressure bubble immersion technique, a twin-sheet roll-fed technique, a pillow-forming technique, a blow-molding technique, an extrusion blow-molding technique, and combinations thereof. Specifically, blow-molding includes expanding a heated parison against surfaces of a mold using compressed gasses. It is also contemplated that multiple blisters may be formed simultaneously using any of the aforementioned techniques, any technique known in the art, and combinations thereof.

In one embodiment, a film or sheet of the composite (10) is unwound from a reel and guided though a pre-heating station on a blister production line that utilizes upper and lower pre-heating plates. The temperature of the pre-heating plates is typically set such that the film or sheet of the composite (10) will warm, soften and become moldable. The warm film or sheet typically then arrives in a forming station where a large pressure (4 to 8 bar) forms the cavity into a negative mold. The negative mold is then cooled such that the film or sheet becomes rigid again and maintains its shape when removed from the mold. In some embodiments, the warm film or sheet is partially pushed down into the negative mold by a "plug-assist" feature.

In one embodiment, the method includes the step of disposing the one or more additional layers on the first and/or second layers (12, 14). The one or more additional layers may be disposed using any means known in the art. Typically, the one or more additional layers are also disposed using thermoforming, lamination, and/or co-extrusion techniques.

The blister may be of any desired shape and is typically formed in the shape of the medical device (16). In various embodiments, the blister is formed in rectangular or hemispherical shapes. After the blister is shaped, the medical device (16) is typically disposed within the blister, i.e. within the cavity, and the blister is preferably sealed with the lid (36). It is contemplated that the blister may define a space such that the medical device (16) is allowed to move within the blister. The blister may also include one or more spacers disposed therein to aid in holding the medical device (16) in place and/or to cushion the medical device (16). In one embodiment, the one or more spacers are further defined as foam spacers, e.g. cross-linked polyurethane foam spacers.

In various embodiments, the thickness of the first and second layers (12, 14) of the composite (10) varies at differing points on the blister or composite. Typically, these thicknesses are correlated to a depth of the cavity (C). For example, in blisters that have deep cavities (C), the thicknesses of the first and second layers (12, 14) may vary to a greater degree than in blisters that have shallow cavities (C). It is believed that the thicknesses of the first and second layers (12, 14) may also be correlated to a chosen method of formation, such as thermoforming. Of course, the instant composite (10) is not limited to these correlations. In various embodiments, the first and second layers have the following approximate gauges (inches):

| Gauge of First Layer (12) | Gauge of Second Layer (14) |
|---|---|
| 0.2500 | 0.2500 |
| 0.0200 | 0.0350 |
| 0.0150 | 0.0350 |
| 0.0200 | 0.0150 |
| 0.0150 | 0.0150 |
| 0.0010 | 0.0010 |
| 0.0005 | 0.0005 |

In other embodiments, one or more of these gauges may independently be different by more than ±1%, 5%, 10%, 15%, 20%, or 25%.

A packaging system for packaging the medical device (16) is also shown in FIG. 8. The packaging system typically includes the composite (10) (e.g. blister) disposed in one or more containers to form a double sterile barrier, e.g. a blister within a blister. The one or more containers may be further defined as films, boxes, cartons, bags, envelopes, drums, cans, bottles, or the like. The one or more containers may be formed from any suitable material known in the art including, but not limited to organic polymers such as acrylics, polyesters, silicones, polyurethanes, halogenated plastics, polystyrene, polyvinylchloride, polyethylene terephthalategycol (PETG), polychlorotrifluoroethylene (PCTFE), low-density polyethylenes, high-density polyethylenes, cross-linked, high-density polyethylenes, polycarbonates, polysulfones, fluorinated ethylene polypropylene, ethylene-tetrafluoroethylene, ethylene-chlorotrifluoroethylene copolymer, perfluoroalkoyl, polypropylene, and combinations thereof. In one embodiment, the one or more containers include PETG. In various other embodiments, the one or more containers may include Tyvek®, a combination of Tyvek® and polyethylene, Surlyn®, or a combination of Surlyn® and Tyvek®.

The one or more containers may be identical to the composite (10) or may be different, e.g., in an embodiment where the one or more containers is identical to the composite (10), the one or more containers include a first container layer and a second container layer identical to the first layer (12) and the second layer (14), respectively, of the composite (10) described in greater detail above. In this embodiment, the first container layer forms a floor (48) having a plurality of container walls extending therefrom, typically including sides (44) and ends (46). The sides and/or ends (44, 46) define a void (V) for receiving the composite (10) and the second container layer is disposed on said first container layer opposite said void (V).

Figure 10:
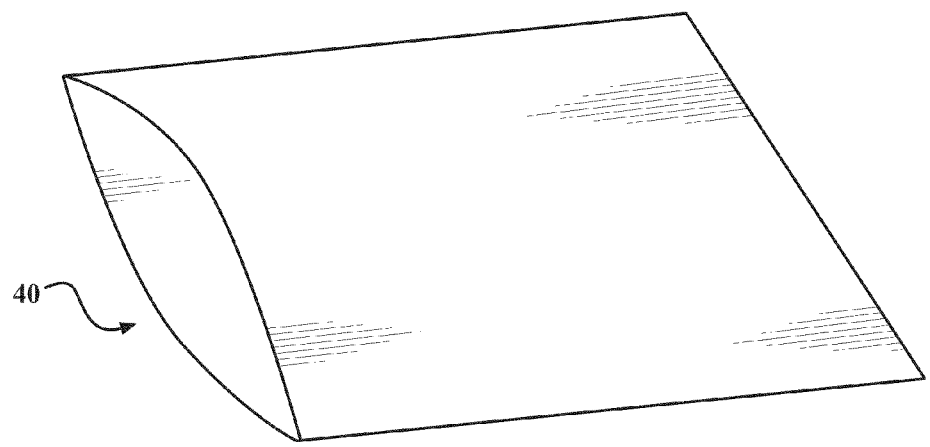
FIG. 10 illustrates one embodiment of the outer container that is further defined as a pouch with one open, but sealable, end.

In one embodiment, as set forth in FIG. 8, the one or more containers is further defined as an outer container (40) that surrounds the composite (10) (e.g. blister). In other words, the composite (10) is disposed within the outer container (40). Said differently, the outer container (40) houses the composite (10). In this embodiment, the outer container (40) is exposed to the environment. In one embodiment, the outer container (40) is further defined as a pouch with one open, but sealable, end, as illustrated in FIG. 10. The open end may be sealed by any means known in the art including physical and/or chemical means. In one embodiment, the end is sealed to create a sterile barrier. In another embodiment, the end is not sealed.

The one or more containers (e.g. the outer container (40)) typically include a body (42) that is integrally formed with a plurality of container walls, including sides (44) and ends (46), and a floor (48), which together define a void (V) in which the composite (10) may be disposed. The sides (44) and/or ends (46) may define top portions (50) ending in flat or planar surfaces (52) that are substantially parallel to the floor (48). In one embodiment, a stepped indentation (54) is formed in one or more of the surfaces and is disposed around the void (V). The stepped indentation (54) typically includes an edge (56) that is beveled upward to the flat or planar surfaces (52). The container also defines a periphery (58).

The container may also include a cover (60) that includes a peripheral edge (62). The cover (60) may be the same as the lid (36) or may be different. Typically, the cover (60) is disposed such that the peripheral edge of the cover (62) aligns with a periphery of the container (58). The cover (60) may be formed from any suitable material in the art that can withstand sterilization with heat, chemicals and/or radiation (e.g. ethylene oxide, gamma, e-beam, and/or peroxides). Suitable materials include, but are not limited to, Tyvek®, metal foils, polymer films, a combination of Tyvek® and polyethylene, Surlyn®, a combination of Surlyn® and Tyvek®, and combinations thereof. Typically, the cover (60) is formed from Tyvek®. The cover (60) typically has a thickness of from 1 to 60 mils but is not limited to this thickness. The cover (60) may have any thickness as chosen by one of skill in the art. The cover (60) may also be of any color, may be clear, opaque, or transparent. The cover (60) may also be smooth or rough or have any texture known in the art.

A packaging system for packaging the medical device (16) in the container is also described. In one embodiment the packaging system includes the container for receiving the medical device (16) and the composite (10). The composite (10) is disposed in the container and contacting the medical device (16). Typically, the composite (10) supports the medical device (16) disposed in the container. In this embodiment, the composite (10) can be defined as a support for the medical device (16) having any suitable configuration. Typically, the composite (10) cradles the medical device (16) and is complementary in shape to the medical device (16).

Both the one or more containers, and the packaging system itself, may be formed by any method or means known in the art. Typically, the one or more containers are formed using thermoforming and/or lamination techniques. However, the instant invention is not limited to such processes. The packaging system is typically formed using a method that includes the step of disposing the composite (10) within the one or more containers (e.g. the outer container (40)). In various embodiments, the method of forming the packaging system includes the steps of sealing the composite (10) and/or the one or more containers.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims, the present invention may be practiced otherwise than as specifically described.

What is claimed is:

1. Packaging for a medical device, wherein said packaging comprises:
    a first layer forming a base having a plurality of walls extending therefrom to define a cavity for receiving the medical device wherein said plurality of walls includes one or more projections for engaging the medical device and said plurality of walls includes a periphery and at least one flange extending from said plurality of walls and disposed about said periphery; and
    a second layer disposed on said first layer opposite said cavity, wherein said second layer is an outermost layer of said packaging and comprises acrylics, polyesters, silicones, halogenated plastics, polystyrenes, polyvinylchlorides, polyethylene terephthalate glycols, polychlorotrifluoroethylenes, low-density polyethylenes, high-density polyethylenes, polyethylene foams, polycarbonates, polysulfones, fluorinated ethylene polypropylenes, ethylene-tetrafluoroethylenes, ethylene-chlorotrifluoroethylene copolymers, perfluoroalkyl plastics, polypropylenes, cyclic olefin copolymers, and combinations thereof;
    wherein said first layer comprises an aromatic polyether polyurethane, is an innermost layer of said packaging, and is disposed to directly contact the medical device, and wherein said aromatic polyether polyurethane has a specific gravity of from 0.84 to 1.40 measured according to ASTM D-792.

2. Packaging as set forth in claim 1 further comprising a lid including a peripheral edge.

3. Packaging as set forth in claim 2 wherein said lid comprises a high density polyethylene.

4. Packaging as set forth in claim 1 wherein said aromatic polyether polyurethane has a shore A hardness of from 66.25 measured according to ASTM D-2240 to a shore D hardness of 70.00.

5. Packaging as set forth in claim 1 wherein said aromatic polyether polyurethane has:
    an ultimate tensile strength of from 7,500 to 12,500 psi;
    an ultimate elongation of from 431.25% to 718.75%;
    a 100% modulus of from 862.5 to 1437.5 psi; and
    a 300% modulus of from 2025 to 3375 psi, each measured according to ASTM D-882.

6. Packaging as set forth in claim 1 wherein said aromatic polyether polyurethane has a tear resistance of from 375 to 625 pli measured according to ASTM D-1004.

7. Packaging as set forth in claim 1 wherein said aromatic polyether polyurethane has a minimum softening point of from 112.5 to 187.5° C. and a maximum softening point of from 127.5 to 212.5° C. measured according to ASTM E2347-04.

8. Packaging as set forth in claim 1 further defined as a blister that has a shape complementary to a shape of the medical device.

9. Packaging as set forth in claim 1 wherein the medical device is further defined as a medical implant.

10. Packaging for packaging a medical device as set forth in claim 1 wherein
    said plurality of walls include a periphery and at least one flange extending from said plurality of walls and disposed about said periphery;
    said second layer comprises a polyethylene terephthalate glycol; and
    said packaging further comprising a lid comprising a high density polyethylene including a peripheral edge.

11. Packaging as set forth in claim 1 wherein the second layer has a thickness of from 0.5 to 250 mils.

* * * * *